(12) United States Patent
Bao et al.

(10) Patent No.: US 7,189,987 B2
(45) Date of Patent: Mar. 13, 2007

(54) ELECTRICAL DETECTION OF SELECTED SPECIES

(75) Inventors: Zhenan Bao, Milburn, NJ (US); Bernard Yurke, Plainfield, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 188 days.

(21) Appl. No.: 10/405,398

(22) Filed: Apr. 2, 2003

(65) Prior Publication Data
US 2004/0195563 A1    Oct. 7, 2004

(51) Int. Cl.
*H01L 51/00* (2006.01)
(52) U.S. Cl. .................. 257/40; 257/252; 257/288; 257/E51.006
(58) Field of Classification Search .............. 257/40, 257/253, 288, 414, 613, 252
See application file for complete search history.

(56) References Cited

U.S. PATENT DOCUMENTS

| 4,881,109 | A |   | 11/1989 | Ogawa |         |
|-----------|---|---|---------|-------|---------|
| 5,571,568 | A | * | 11/1996 | Ribi et al. | 427/487 |
| 6,096,825 | A |   | 8/2000  | Garnier |       |
| 6,203,981 | B1| * | 3/2001  | Ackley et al. | 435/6 |
| 6,545,758 | B1| * | 4/2003  | Sandstrom | 356/317 |

| 2002/0006889 | A1 | * | 1/2002  | Wurtz et al. | 510/421 |
| 2002/0167003 | A1 |   | 11/2002 | Campbell et al. | |

FOREIGN PATENT DOCUMENTS

| EP | 1 085 319 A1 | 3/2001 |
| JP | 05312746     | 11/1993 |
| JP | 10260156     | 9/1998 |
| WO | WO 97/27316  | 7/1997 |

OTHER PUBLICATIONS

Garnier; New Generation of Organic-Based Thin-Film Transistors; Device Research Conference, 1995. Digest. 1995 53rd Annual, Jun. 19-21, 1995; pp. 8.*
Assadi, et al.; "Determination of Field-Effect Mobility of Poly (3-Hexylthiophene) Upon Exposure to NH3 Gas"; Synthetic Metals, Elsevier Sequoia, vol. 37, 1990, pp. 123-130.
Kymissis, et al.; "High-Performance Bottom Electrode Organic Thin-Film Transistors"; IEEE Transactions on Electron Devices, vol. 48, No. 6, Jun. 2001, pp. 1060-1064.
Kumar, et al.; "Advances in Conductive Polymers"; Elsevier Science Ltd., Eur. Polym. Journal, vol. 34, No. 8, Aug. 1, 1998, pp. 1053-1060.

(Continued)

*Primary Examiner*—Marcos D. Pizarro

(57) ABSTRACT

The present invention provides an organic field effect transistor and a method of fabricating the transistor. The transistor includes a semiconductive film comprising organic molecules. Probe molecules capable of binding to target molecules are coupled to an outer surface of the semiconductive film such that the interior of the film being substantially free of the probe molecules.

15 Claims, 6 Drawing Sheets

OTHER PUBLICATIONS

Fine D., et al. ; "Organic FET Chemical Sensors with Small Molecule Receptors", Abstract Submitted for the Mar. 2003 Meeting of The American Physical Society; www.eps.org/aps.meet/MAR03/baps/abs/G7760001.html.

C. Bartic, A. Campitelli and S. Borghs; "Field-Effect Detection of Chemical Species with Hybrid Organic/Inorganic Transistors"; Applied Physics Letters, vol. 82, No. 3, Jan. 20, 2003; pp. 475-477.

Howard E. Katz, Joyce G. Laquindanum and Andrew J. Lovinger; "Synthesis, Solubility and Field-Effect Mobility of Elongated and Oxa-Substituted Dialkyl Thiophene Oligomrs, Extension of "Polar Intermediate" Synthetic C Strategy and Solution Depositio n on Transistor Substrates"; American Chemical Society Chem. Mater 1998, 10, pp. 633-638.

Todd Thorsen, Sebastian J. Maerkl, Stephen R. Quake; "Mocrofluidic Large-Scale Integration"; Science vol. 298; Oct. 18, 2002; pp. 580-584.

H. Korri-Youssoufi, F. Garnier, P. Srivastava, P. Godillot and A. Yassar; "Toward Bioelectronics: Specific DNA Recognition Based on an Oligonucleotide-Functionalized Polyyrrole"; Journal American Chem. Society 1997, 119, pp. 7388-7389.

* cited by examiner

ELECTRICAL DETECTION OF SELECTED SPECIES

TECHNICAL FIELD OF THE INVENTION

The present invention is directed, in general, to the electrical detection of selected species, in particular biologically relevant species. More specifically, the invention is directed to a biosensor device that includes an organic field effect transistor and a method of manufacturing the device.

BACKGROUND OF THE INVENTION

There is great interest in the rapid simultaneous detection of large numbers of biological species such as naturally occurring DNA, RNA, proteins, and other naturally occurring molecules, as well as man-made aptamers, synthetically modified proteins or toxins. Advances in biosensor technology have facilitated numerous potential medical applications, such as drug discovery, detecting genetic mutations and evaluating the effect of gene therapy or the identification of biological toxins.

For instance, traditional radio-immunoassay approaches to detecting proteins, hormones and various pathogens involve the binding of antibodies to a solid support to form a micro array and then exposing the analyte to the array of antibodies. The analysis of DNA fragments similarly involves fixing single stranded target DNA fragments, representing the genome of an organism, for example, to individual wells in a solid support to form a micro array. Such DNA micro arrays, also known as DNA chips, provide a highly sensitive means of detecting specific target DNA fragments. The micro array is analyzed by exposing target DNA fragments to fluorescently labeled probes of cDNA or mRNA of unknown identity. When the nucleic acid sequence of the probe cDNA or mRNA is complementary to the nucleic acid sequence of the target DNA, the probe cDNA or mRNA hybridizes to the DNA fragment. The flourescent label attached to the cDNA or mRNA is then detected with the aid of lasers and sensitive fluorescence detection equipment.

The wide-spread application of such DNA micro arrays and other types of arrays is limited by a number of factors, however. For example, the micro arrays and the fluorescently labeled cDNA and mRNA probes are expensive to produce or purchase. The high cost of lasers to initiate fluorescence, detection equipment, such as confocal microscopes and flourescent light detection equipment, also limit wide-spread applications of this technology. In addition, the shear bulk of such equipment limits the physical location where DNA micro arrays can be analyzed.

Electrical biosensor devices have been proposed as an alternative means for detecting DNA and RNA. An electrical readout corresponding to the concentration of a target molecule in a particular assay solution would allow a substantial reduction in the size and cost of the equipment needed to apply micro array technology. Previous biosensor devices have used an electrode comprising a semiconductive film made of organic polymers functionalized with selected species of probe oligonucleotides of single stranded nucleic acid sequences. Alternatively, monomers of the organic polymer are functionalized and then polymerized to form the functionalized organic polymer. In either case, the probe oligonucleotides are attached as side chains to the organic polymers. Semiconductive films are then made of the functionalized organic polymers. When exposed to a liquid containing the appropriate complementary target nucleic acid sequence, the probe and target nucleic acid sequence hybridize, thereby causing a detectable change in the conductivity of the functionalized organic polymers incorporated into the semiconductive film.

One objective of the invention is to provide sensitive electrical devices for the detection of a variety of target biological species. Another objective of the invention is to provide a method for the fabrication of such devices.

SUMMARY OF THE INVENTION

The present invention recognizes that the practical application of such electric devices has been limited due to poor sensitivity, in part, because functionalizing the side-chains of the organic polymer reduces the polymer's conductivity. Moreover, the binding of the target biomolecules to the probe molecules attached throughout the organic polymer does not result in a sufficiently large change in conductivity to allow the detection of small quantities of the target biomolecule.

To address these deficiencies, one embodiment of the present invention provides an organic field effect transistor for the detection of biological target molecules. The transistor includes a semiconductive film comprising organic molecules. In addition, a probe molecule is coupled to an outer surface of the semiconductive film, the film having an interior substantially free of the probe molecules.

In another embodiment, the invention further provides a method of fabricating an organic field effect transistor for the detection of biological target molecules. The method comprises forming a transistor channel that includes forming a semiconductive film comprising organic molecules between a source and drain. Forming the transistor channel also includes coupling a probe molecule to an outer surface of the semiconductive film, the semiconductive film having an interior substantially free of the probe molecule Still another embodiment of the invention is a biosensor system for the detection of biological target molecules. The biosensor system comprises a biosensor device, a sample, and an assay system. The biosensor device includes one or more organic field effect transistors, each of the transistors including a transistor channel. The channel in turn comprises a semiconductive film comprising organic molecules; and probe molecules coupled to an outer surface of the semiconductive film, such that the semiconductive film has an interior substantially free of the probe molecules. The sample is capable of holding a target molecule that is configured to bind to with one or more of the probe molecules. The assay system is configured to bring the biosensor device in contact with the sample.

BRIEF DESCRIPTION OF THE DRAWINGS

The invention is best understood from the following detailed description, when read with the accompanying FIGUREs. Various features may not be drawn to scale and may be arbitrarily increased or reduced for clarity of discussion. Reference is now made to the following descriptions taken in conjunction with the accompanying drawings, in which.

DETAILED DESCRIPTION

The present invention benefits from the realization that previous biosensors for detecting biological target molecules have poor conductivity because probe molecules are attached to the interior side-chains throughout the organic polymers of the semiconductive film in the biosensor. Probe molecules comprising nuclei acid or amino acid sequences, such as DNA or proteins, impede the formation of ordered semiconductive films composed of the functionalized organic polymers. This, in turn, detrimentally decreases the efficiency of charge transfer between the semiconductive organic polymers of the semiconductive film. Moreover, the present invention recognizes that probe molecules, such as DNA, have substantial insulating properties when they are incorporated throughout the interior of such films, thereby further decreasing the conductivity of the films.

The present invention further recognizes the advantages of forming biosensor devices having a semiconductive film that includes electrically conducting organic molecules with probe molecules attached substantially to the outer surface of the film. The complete or substantial absence of probe molecules in the interior of the film facilitates the formation of uniform closely packed crystalline or polycrystalline films of the organic molecules. This is advantageous because the charge transfer characteristics of the film depends on the efficient packing of the organic molecules, which generally have one or more conjugated Pi bonds, to form a system of conjugated Pi bonds. The efficiency of charge transfer from one organic molecule to another increases as the distance between the conjugated Pi bonding systems of adjacent organic molecules is decreased.

Figure 1:
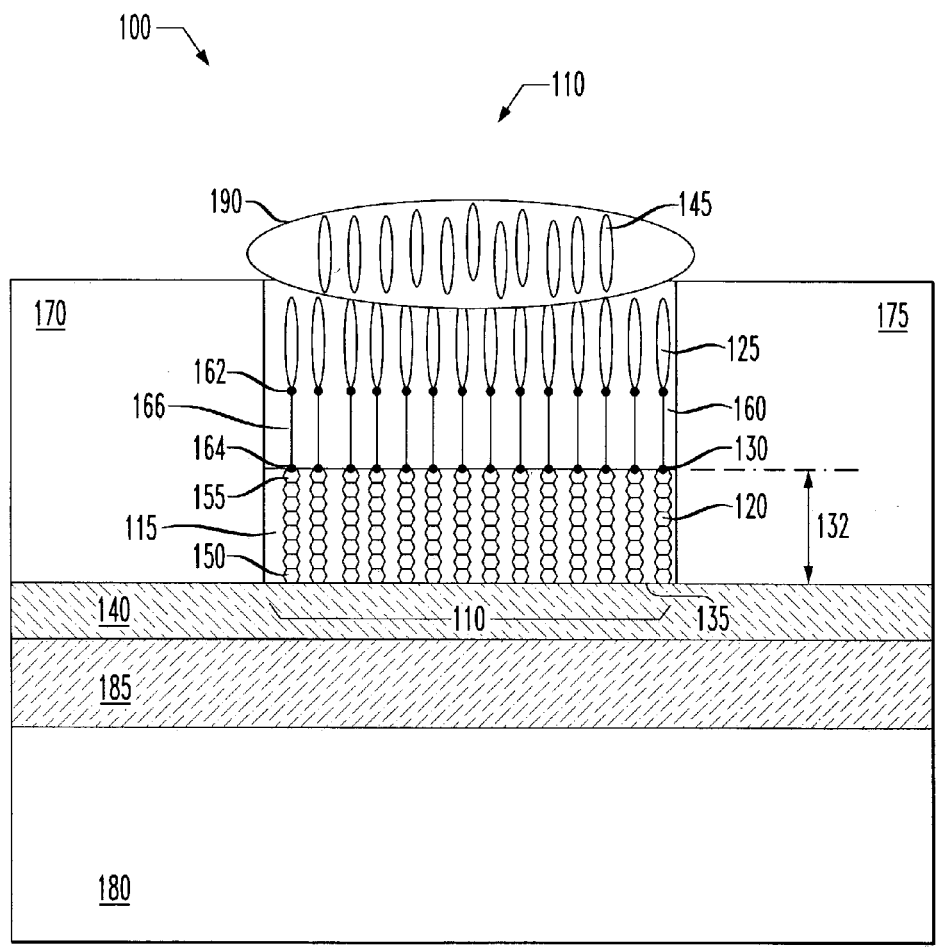
FIG. 1 schematically illustrates a detailed sectional view of an organic field effect transistor of the present invention.

FIG. 1 illustrates a schematic representation of a portion of an organic field effect transistor 100 for the detection of biological target molecules. The transistor 100 comprises a transistor channel 110 having a semiconductive film 115 comprising organic molecules 120. The transistor 100 further includes probe molecules 125 coupled to an outer surface 130 of the semiconductive film 115, the film 115 having an interior substantially free of, if not completely void of, the probe molecules 125. For the purposes of the present invention the term substantially free of probe molecules refers to the film's 115 interior having, at most, trace amounts of probe molecules 125 present therein. For instance, in embodiments where the organic molecules 120 are hydrophobic, then hydrophilic probe molecules 125, such as certain nucleic acid or amino acid sequences, will be excluded from the film's interior. In such embodiments, the trace amounts of probe molecules 125 in the film's interior 115 would be less than or equal to the solubility of the probe molecule 125 in the organic molecule 120.

In preferred embodiments, organic molecules 120 have a conjugated pi system of bonds, although any semiconductive materials having organic molecules 120 are within the scope of the present invention. Preferably, the organic molecules 120 of the film 115 have an ordered crystalline or polycrystalline structure. The organic molecules 120 can be any carbon containing compounds capable of forming a semiconducting film 115. More preferably, the organic molecules 120 have a high field effect mobility (i.e., greater than about $10^{-4}$ cm$^2$/V•s). Even more preferably, the organic molecules 120 have a field effect mobility of greater than about $10^{-2}$ cm$^2$/V•s, such as that provided by molecules having a conjugated pi system, as exemplified by oligothiophene or polythiophene.

In certain preferred embodiments, the organic molecules 120 are oligomers. Oligomers are more desirable than certain substituted polymers due to the better ability of oligomers to form ordered crystalline films having no probe molecules 125 in their interior. For the purposes of the present invention, the term oligomer as applied to the organic molecules 120 of the semiconductive film 115 referred to molecules having from 2 to 100 repeating units. The term polymer refers to organic molecules 120 having greater than 100 repeating units. In certain preferred embodiments the organic molecule 120 is an oligomer having from 4 to 20, and even more preferably, from 4 to 10 repeating units.

For example, an oligothiophene has between 2 and 100 repeating units of thiophene while polythiophene has greater than 100 repeating units of thiophene. In one preferred embodiment, the organic molecule 120 is sexithiophene, and more preferably alpha sexithiophene. Other semiconductive organic compounds, however, are also within the scope of the present invention. Nonlimiting examples include oligophenyl or polyphenyl compounds. The organic molecule 120 may also comprise combinations of different benzoid aromatic ring structures like benzene, napthalene or anthracene rings coupled to each other such as in such as pentacene, nonbenzoid aromatic rings, or heterocylic rings, such as thiophene.

The semiconducting film 115 may comprise a single molecular layer of the organic molecule or multiple layers of organic molecules. The film may have a thickness 132 of about 20 Angstroms or higher. In a preferred embodiment, the film 115 has a thickness 132 between about 20 and about 100 Angstroms. In certain embodiments where the organic molecules 120 of the film 115 comprise sexithiophene, the film's thickness 132 corresponds to one to three molecular layers of sexithiophene.

A thin film 115, such as a thickness 132 in the above-cited range, is preferred because the resulting biosensor device is expected to be more sensitive. This follows because the current passing through the semiconducting film 115 is thought to flow primarily at the interface 135 between an insulating layer (e.g., a gate dielectric) 140, and the semiconducting film 115. The closer the probe molecules 125 are to that interface 135, the more sensitive the transistor 100 will be to changes in channel conductivity or channel mobility associated with the binding of a target molecule 145 to the probe molecule 125. In particular, one or both of channel conductivity or channel mobility changes due to the binding of target molecules 145 to the probe molecules 125 thereby providing a method for detecting the target molecules 145.

In certain embodiments, where an ultra thin film 115 is desired (e.g., thickness 132 of less than about 30 Angstroms), the semiconducting film 115 preferably comprises a monolayer of the organic molecule 120. In some embodiments, it is preferable to covalently attach the organic molecules 120 to the underlying insulating layer 140. In such embodiments, the end of the organic molecule 150 opposite to the end that is coupled to the probe molecule 155 is functionalized to facilitate covalent attachment to the insulating layer 140. If the insulating layer 140 is silicon dioxide, for example, the end of the organic molecule 150 can be functionalized with a silane moiety.

In still other embodiments, it is advantageous for the semiconducting film to further include linker molecules 160 coupled to the end of the organic molecule 155 situated at the outer surface of the film 130. One or more functional groups 162, 164 attached to the linker molecule 160 facilitates the coupling of probe molecules 125 to the organic molecules 120, as further discussed below. Coupling can involve covalent or non-covalent interactions between the linker molecule 160 and the organic molecule 120 or probe molecule 125. The linker molecule 160 may also have one or more spacer groups 166 that serve to separate the probe molecule from the organic molecule when these molecules are coupled to each other. A spacer group 166 is desirable in instances where the functional groups 162, 164 used to facilitate coupling of probe molecules 125 to the organic molecules 120 could detrimentally affect the electrical properties of the semiconducting film 115. Moreover, a spacer group 166, preferably attached to the organic molecule 120 before deposition, by separating the probe molecule 125 from the organic molecule 120, can facilitate a uniform ordered packed structure so that the film 115 retains its conductive properties after being coupled to the probe molecules 120. In addition, by adjusting the length of the spacer group 166 it is possible to advantageously increase or decrease the affect that the binding of the target molecule 145 to the probe molecule 120 has on the conductive properties of the film 115, for example, by changing the distance between charged target molecules 145 and the film 115. Another advantageous feature is that the linker molecule 160 can provide electrical insulation between the semiconducting film 115 and the aqueous solution containing the target molecules 145. In certain embodiments, therefore, attaching the target molecule 145 does not perturb the electrical properties of the organic molecule 120.

Examples of suitable linker molecules 160 include compounds having amino or thiol functional groups 162 covalently attached to a spacer group 166. In certain preferred embodiments, the spacer group 166 is an alkyl chain having up to 20 carbon atoms. In one embodiment, the linker molecule 160 has an amino functional group 162 attached to one end of a spacer group 166 of n-hexane. The other end of the n-hexane spacer group 166 is attached to an organic molecule 120 of sexithiophene at the carbon 5 position in the terminal thiophene ring, as facilitated by a functional group 164. Alternatively, there may be no functional group 164 on the end of the linker molecule adjacent to the organic molecule 120. For instance, the n-hexane spacer group 166 can have non-covalent interactions with the organic molecule 120 that serve to couple the linker molecule 160 to the organic molecule 120. In other preferred embodiments, the linker molecule 160 comprises a layer of an organic polymer such as polyimide, or an inorganic polymer, such as silicon dioxide. In such embodiments, for example, the linker molecules 160 can include an amino or thiol functional group 162 attached to a layer of spacer groups 166 comprising silica formed by depositing amino-silane or thiol-silane on the layer of spacer groups 166.

The probe molecule 125 can be any molecule capable of being coupled to the organic molecules 120 of the semiconductive film 115 and capable of binding to a specific target molecule 145 or class of target molecules 145. In certain preferred embodiments, the probe molecule 125 comprises nucleic acid or amino acid sequences, such as DNA or proteins. In other preferred embodiments, the probe molecule 125 is a single stranded DNA having a nucleic acid sequence that is complementary to at least a portion of the nucleic sequence of the target molecule 145. Other embodiments of the probe molecule 125 include RNA or aptamers. In still other embodiments the probe molecule 125 is a protein, such as an antibody or antibody fragment having a high affinity for a target protein 125.

Preferably the target molecule 145 is a biological molecule. In certain embodiments, the target molecule 145 has a net positive or negative charge. In certain preferred embodiments the target molecule 145 is cDNA or mRNA that is complementary to the probe molecule 125. In such embodiments, the target molecule 125 has a net negative charge. In other embodiments the target molecule 145 is an antigen to the probe molecule 125. When charged target molecules 145 bind to the probe molecules 125 that are coupled to the organic molecules 120 of the semiconductive film 115, the static charge in the vicinity of the semiconductive film 115 changes. This, in turn, changes the electrical field experienced by the semiconductive film 115. As a result of the change in the electrical field, the flow of current between source and drain electrodes 170, 175 of the transistor 100 changes in proportion to the change in the electrical field experienced by the channel 110. Under fixed environmental conditions (e.g., constant pH, temperature and ionic strength), the extent of change in the electrical field is proportional to the number of the target molecules 145 that bind to the probe molecules 125.

In other embodiments however, the target molecule 145 has no net charge. When a neutral target molecule 145 binds to the probe molecule 125, the dielectric constant in the vicinity of the semiconductive film 115 changes. This, in turn, changes the capacitance between the fluid containing the target molecules 145 and the film 115. This results in a change in the effective gate capacitance which, by changing the electrical field in the semiconductive film, can be detected as a change in the conductivity of the semiconductor film 115. Consider, for example, when the target molecule 145 is a protein with a net charge of zero. When the neutral target protein 145 binds to the probe molecule 125, water molecules associated with the probe molecules 125 are excluded from the semiconductive film's outer surface 130, resulting in a change in dielectric constant in the vicinity of the probe molecule 125 and adjacent region of film 145.

Preferred embodiments of organic field effect transistor 100 further include a substrate 180 under the channel 110, a gate 185 over the substrate 180, with the above mentioned insulating layer 140 over the gate 185 and the above-mentioned source and drain 170, 175 over the insulating layer 140, with the channel 110 located between the source and drain 170, 175. In certain preferred embodiments, the sensitivity of the change in conductivity or mobility of the active channel associated with the binding/unbinding of a target molecule 145 to the probe molecule 125 depends on the voltage applied to the gate 185. However, the organic field effect transistor 100 can be configured in other ways well known to those of ordinary skill in the art.

In operation, the portion of the transistor above the channel is exposed to an assay solution 190 containing analytes that may include the target molecule 145. For example, the assay solution 190 may be an aqueous solution that includes buffers, electrolytes and target molecule 145. In some embodiments a voltage is applied to the drain 175 and the gate 185 with the source 170 held at ground. In other embodiments a voltage is also applied to the assay solution 190. Preferably the applied voltage is up to about 10 Volts, and more preferably up to about 2 Volts. In one embodiment, the change in electrical field in the vicinity of the channel that is associated with the binding of a target molecule 145 to a probe molecule 125 results in a change in the voltage between the source and drain, 170, 175 of at least about 0.01 Volts, and more preferably at least about 0.1 Volts. The corresponding change in current between the source and drain, 170, 175 may be about 1000 to 1500 times lower in the presence of the target molecule 145 than the current in the absence of the target molecule 145. One skilled in the art would understand, however, that the minimal acceptable change in voltage between the source and drain, 170, 175 will depend on the smallest current that can be detected. The detection of current changes will involve other factors such as the electronic noise floor, device stability and averaging time.

Figure 2A:
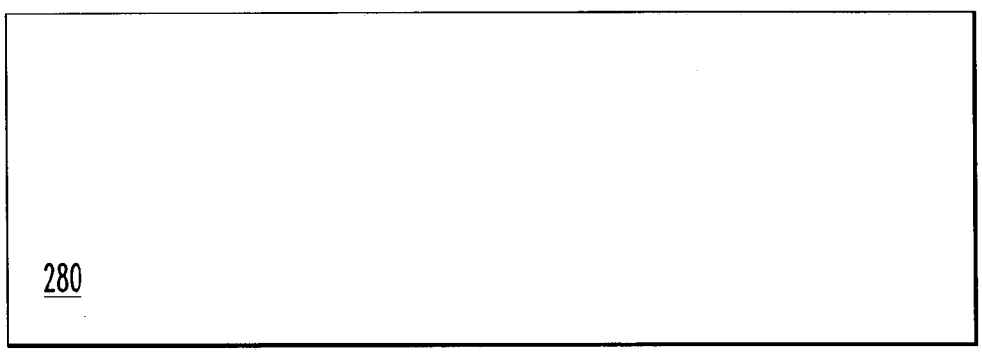
FIGS. 2A to 2F schematically illustrate sectional views of an organic field effect transistor of the present invention at various stages of manufacture.

FIGS. 2A to 2F illustrate selected steps in another embodiment of the present invention, a method of fabricating an organic field effect transistor 200 for the detection of biological target molecules, similar to that described above. Analogous features of the transistor 200 are depicted using similar numerical reference numbers as used in FIG. 1. As illustrated in FIG. 2A, the method includes providing a conventional substrate 280 comprising, for example, a silicon wafer.

Figure 2B:
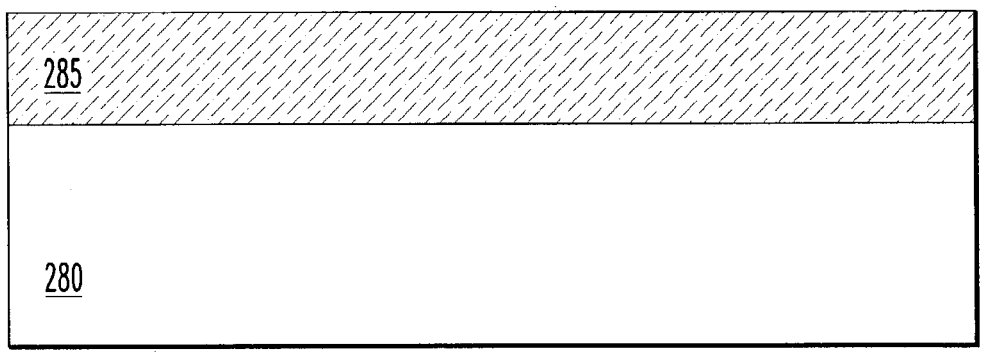

As illustrated in FIG. 2B, a gate 285 is formed over the substrate 280. Suitable conductive gate materials include metals, such as gold, or conducting polymers, such as doped polythiophene. The gate 285 may be deposited by conventional techniques such as chemical vapor deposition, physical sputtering or electron beam evaporation processes. Alternatively, the material used to form the gate 285 may comprise a portion of the substrate, for example silicon doped with a conventional dopant such as boron or phosphorus thereby making a portion of the substrate 280 conductive. As further discussed below, for embodiments where multiple organic field effect transistors 200 are desired, the gate material is later patterned using standard photolithographic techniques to form an array of gates, which are not individually illustrated.

Figure 2C:
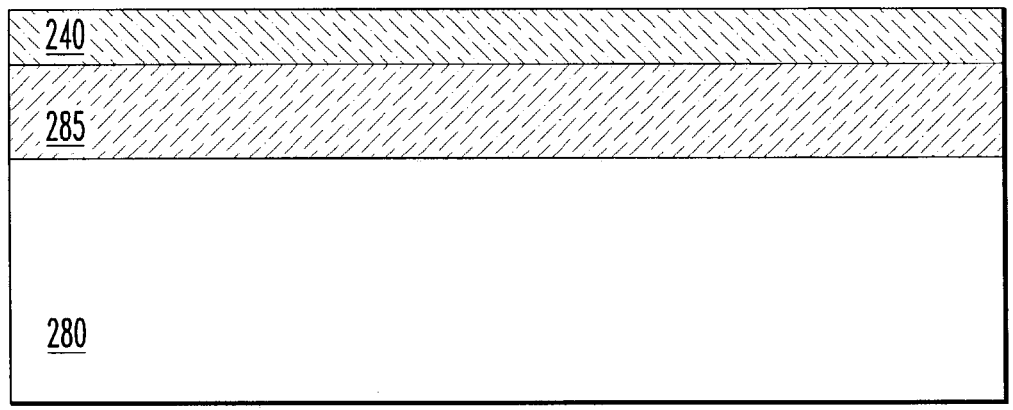

As illustrated in FIG. 2C, an insulating layer 240 is then deposited over the gate 285. Suitable materials for the insulating layer 240 include dielectric materials such as silicon dioxide or polyimide. The insulating layer 240 is deposited using conventional processes such as chemical vapor deposition using tetraethylorthosilicate or thermal growth on a doped silicon gate. The insulating layer 240 is conventionally patterned when the individual gates are patterned.

Figure 2D:
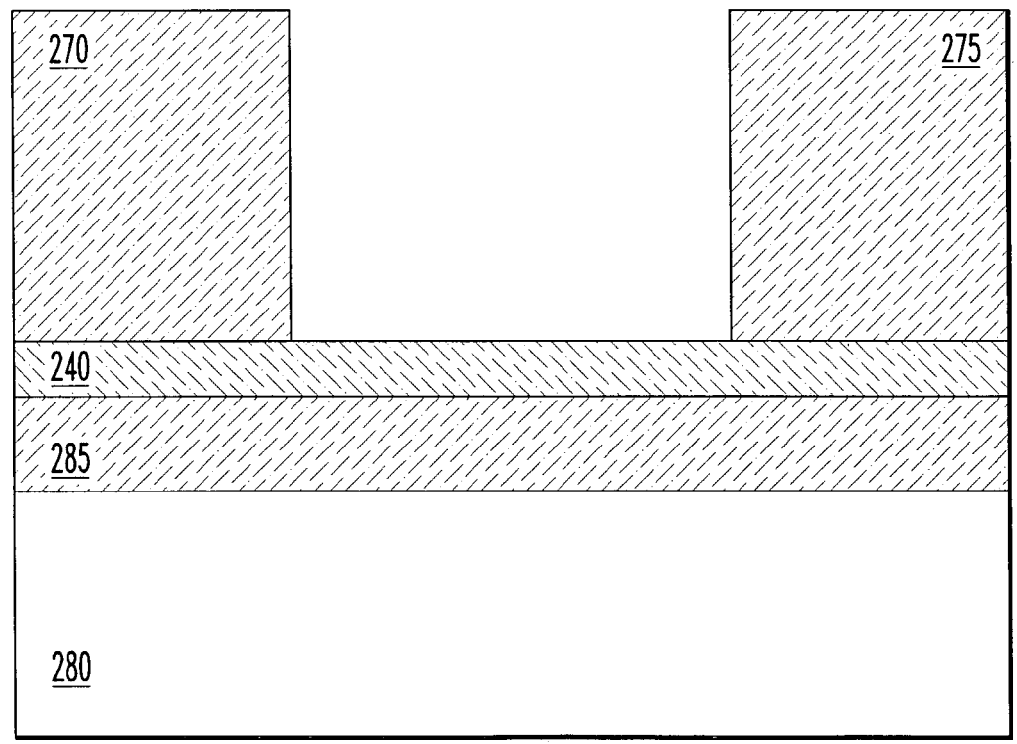

As illustrated in FIG. 2D, a source and drain 270, 275 are formed over the insulating layer 240. The source and drain 270, 275 can comprise metals or conducting polymers similar to polymers used for the gate 285. Similar processes as used to form the gate 285 can also be used for depositing the source and drain material and then using patterning techniques to form the source the drain regions 270, 275 so as to accommodate one or more channel regions 210 of the device 200.

Figure 2E:
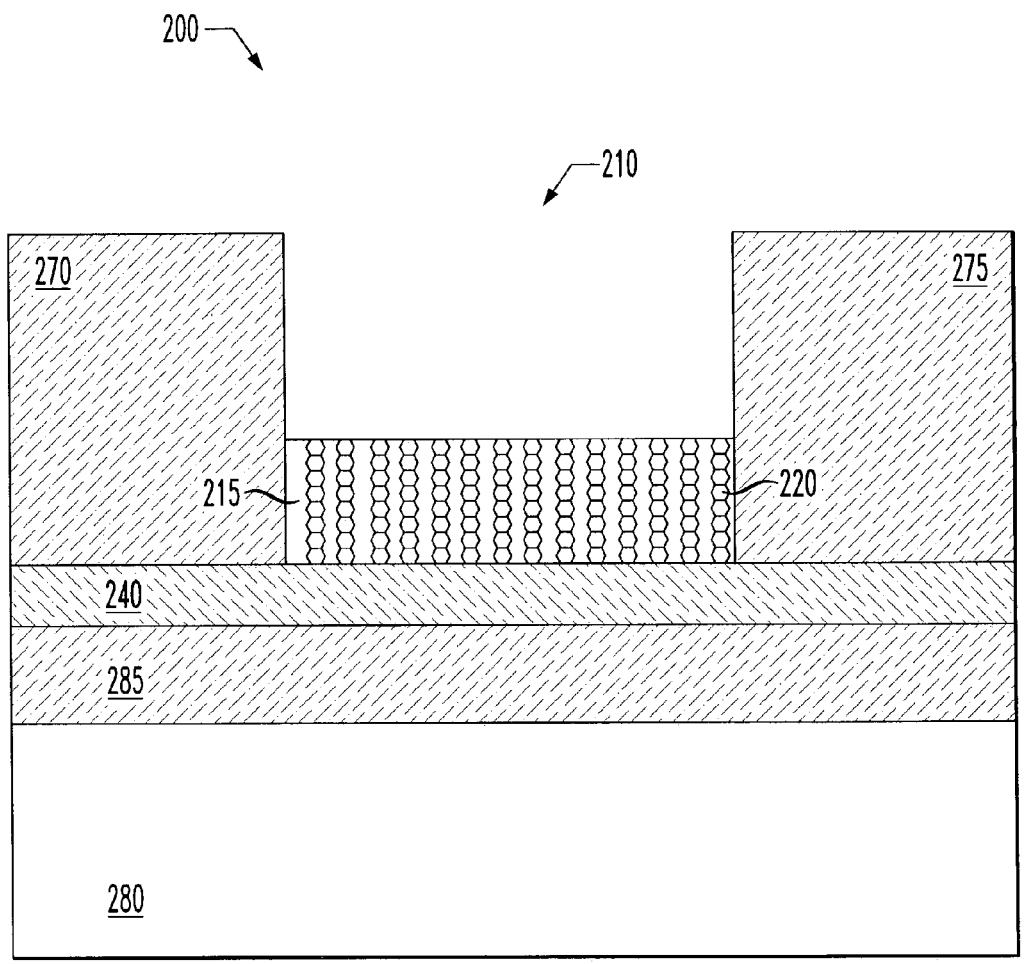

As illustrated in FIG. 2E, forming a transistor channel 210 includes forming a semiconductive film 215 comprising organic molecules 220 between the source and drain 270, 275. Preferably the semiconducting film 215 comprising the organic molecule 220 is formed over the substrate 280 and more preferably on the insulating layer 240. When the organic molecule 220 is an oligomer, the film is preferably formed via vacuum sublimation. Typically, vacuum sublimation is conducted at pressures between about $1 \times 10^{-4}$ to $1 \times 10^{-6}$ Torr, using conventional procedures well known to those skilled in the art. Vacuum sublimation is preferred because of the relative simplicity of this procedure. Vacuum sublimation, for example, does not require additional steps to functionalize the organic molecule 220 to make it more soluble in a solvent suitable for spin coating.

If the selected organic molecule 220 is not amenable to vacuum sublimation, and the organic molecule 220 is at least slightly soluble in organic solvents, such as chloroform toluene or xylenes, then alternative conventional procedures such as solution spin coating, vapor deposition or printing may be used. In certain cases it may be desirable to functionalize the organic molecule 220, such as polythiophene, to improve its solubility in the solvent used for spin coating. An example of such functionalization is regioregular poly(3-hexylthiophene).

Figure 2F:
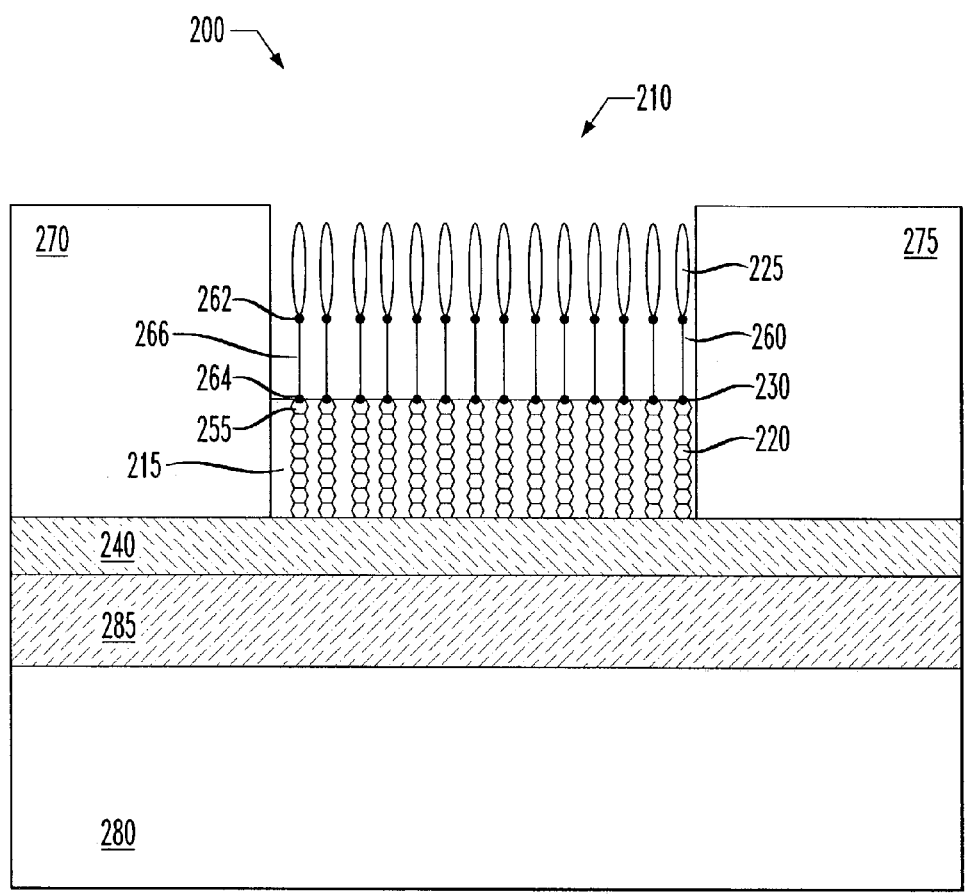

As illustrated in FIG. 2F, forming the channel 210 also includes coupling a probe molecule 225 to an outer surface 230 of the semiconductive film 215 in a manner that causes the semiconductive film 215 to have an interior that is substantially free of the probe molecules 225. Coupling between the probe molecule 225 and the organic molecule 220 of the film 215 is achieved using any number of conventional methods well known to those of ordinary skill in the art. Exemplary methods include those described by Korri-Youssoufi, H., et al., J. Am. Chem. Soc. 119:7388–89 (1997) and Katz, H. E., et al. Chem. Mater. 10:633–38 (1998), which are incorporated herein in their entirety.

For instance, a functional group 264 can be attached to one end 255 of the organic molecule 220 to facilitate coupling to the probe molecule 225. In certain instances, it may be desirable to protect the functional group 264 attached to the organic molecule 220 during the formation of the film 215. Afterwards, the functional group 264 is de-protected to expose the functional group for reaction with the probe molecule 225. Analogous considerations apply to the attachment of a functional group 262 to the probe molecule 225, and the inclusion of an optional spacer group 266 between the functional groups.

Consider an embodiment where, for example, the organic molecule 220 is sexithiophene and the probe molecule 225 is a single stranded oligmer of DNA or RNA. The probe DNA or RNA 225 can be coupled to the film 215 by reacting an amino functional group 262 attached to one end 255 of the organic molecules 220 of the film 215 to acidic groups of the probe DNA or RNA 225 to form an amide bond. Alternatively, a thiol functional group 264 attached to one end 255 of the organic molecule 220 can react with a thiol group present in the probe molecule 225 to form a disulphide bond that couples the probe molecule 225 to the film 215. As indicated above, the thiol group 264 may be protected via acetylation to produce a thiol ester (e.g., $CH_3$—CO—S—R, where R is the organic molecule 220 or a linker group 260 coupled to the organic molecule 220 as discussed above) during the formation of the film 215, and then de-protected by exposure to ammonium hydroxide.

In some embodiments, it is preferable for the coupling between the probe molecules 225 and semiconductive film 215 to be carried out in a solvent that the organic molecules 220 of the film 215 are not soluble in. Examples of suitable solvents include water, or organic solvents like ethanol and acetonitrile. The use of such organic solvents helps to prevent diffusion of the probe molecules 225 into the interior of the film 215 during the reaction to couple the probe molecules 225 to the outer surface of the film 230. In certain embodiments it is desirable for the organic molecule 220 to be an oligomer such as sexithiophene, because oligomers tend to be less soluble in such organic solvents as compared to polymers such as polythiophene.

As noted above, forming the channel 210 includes coupling the probe molecule 225 to the outer surface of the semiconductive film 230. By forming the film 215 of organic molecules 220 prior to coupling the probe molecules 225 to the organic molecules 220, one can ensure that the interior of the film 215 is substantially free of probe molecules 225. Preferably, the probe molecules 225 couple to the organic molecules 220 situated at the outer surface of the film 230.

More preferably, the probe molecules 225 are coupled to the ends of the organic molecules that are closest to the external surface of the film 230. In certain preferred embodiments, as further discussed below, there are multiple transistors 200 each having different probe molecules 225 coupled to their associated channels 210, thereby forming an array of different field effect transistors 200 fabricated on a single substrate 280. In such embodiments, it is desirable to use ink-jet printing technology or microfluidic devices to deposit the different probe molecules 225 on the channels 210 located in the array.

Figure 3:
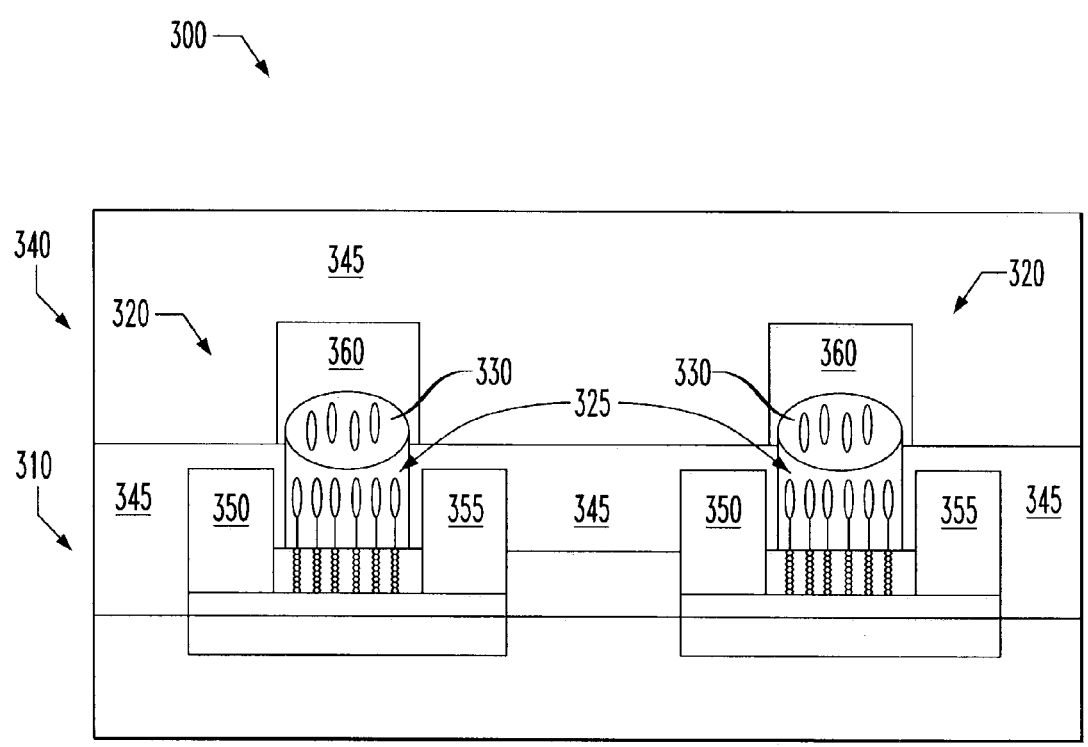
FIG. 3 schematically illustrates detail sectional views of the biosensor system of the present invention.

FIG. 3 illustrates yet another embodiment of the present invention, a biosensor system 300 for the detection of biological target molecules. The system 300 includes a biosensor device 310 that includes a plurality of organic field effect transistors 320. The transistors 320 have a channel 325 comprising a semiconductive film and probe molecules coupled to an outer surface of the semiconductive film, as presented above. In certain embodiments, the transistors 320 have different types of probe molecules in each channel 325 that are capable of binding to different types of target molecules 330. Any of the above-discussed embodiments of the transistor 320 and target molecules 335 discussed above may be included in the system 300.

The system further includes an assay system 340 configured to bring the biosensor device 310 in contact with the sample 330. The assay system 340 may comprise a manual or robotically operated fluidic workstation having multiple print heads, well known to those skilled in the art, for loading probe molecules and samples into the transistors of the biosensor. More preferably, as illustrated in FIG. 3, the assay system 340 comprises a micro fluidic network 345 coupled to the transistors 320, the network 345 capable of electrically isolating the channels of the transistors from remaining components of the transistor, such as the source and drain 350, 355 of the transistor. In other preferred embodiments, the micro fluidic network 345 has conduits 360 that direct multiple samples to discrete transistors 320 of the biosensor device 310 for simultaneous or parallel analysis of the samples. Such networks may comprise elastomeric silicones, such as polydimethylsiloxane, and are formed using procedures well-known to those skilled in the art, e.g., as described by Thorsen et al., Science 298:580–584 (2002), incorporated herein in its entirety.

Although the present invention has been described in detail, those of ordinary skill in the art should understand that they can make various changes, substitutions and alterations herein without departing from the scope of the invention.

What is claimed is:

1. A biosensor system for the detection of biological target molecules comprising:
   a biosensor device, including:
   one or more organic field effect transistors each of said transistors including a channel comprising:
   a semiconductive film comprising organic molecules; and probe molecules capable of binding to target molecules coupled to an outer surface of said semiconductive film, said semiconductive film having an interior substantially free of said probe molecules
   wherein said organic molecules are hydrophobic and said probe molecules are hydrophilic;
   a sample capable of holding said target molecules; and
   an assay system configured to bring said biosensor device in contact with said sample.

2. The biosensor system as recited in claim 1, wherein said assay system comprises a micro fluidic network coupled to said transistors, said network capable of electrically isolating said channel from remaining components of said transistors.

3. The biosensor system as recited in claim 2, wherein said micro fluidic network is configured to direct multiple said sample to individual ones of said transistors of said device for parallel analysis of said samples.

4. An organic field effect transistor for the detection of biological target molecules comprising:
   a transistor channel having a semiconductive film comprising organic molecules and probe molecules coupled to an outer surface of said semiconductive film, said film having an interior substantially free of said probe molecules
   wherein said organic molecules are hydrophobic and said probe molecules are hydrophilic.

5. The transistor as recited in claim 1, wherein said organic molecules have a conjugated pi bond.

6. The transistor as recited in claim 1, wherein said organic molecules are selected from the group consisting of polythiophene and oligothiophene.

7. The transistor as recited in claim 1, wherein said semiconductive film is crystalline or polycrystalline.

8. The transistor as recited in claim 1, wherein said semiconductive film comprises a monolayer of said organic molecules, wherein one end of said organic molecules is coupled to an gate dielectric located below said semiconductive film.

9. The transistor as recited in claim 1, wherein said transistor channel is an active channel, and wherein said probe molecules are capable of binding to target molecules and are chemical bonded to said outer surface.

10. The transistor as recited in claim 1, wherein said probe molecules are selected from the group consisting of: single stranded DNA; RNA aptamers; and proteins, and are configured to bind to biological target molecules selected from the group consisting of: cDNA; mRNA; and antibodies.

11. The transistor as recited in claim 1, wherein binding a target molecule to said probe molecule results in a change in a conductivity or mobility of said channel.

12. The transistor as recited in claim 1, wherein an amount of said probe molecules in said interior is less than or equal to a solubility of said probe molecule in said organic molecule.

13. The transistor as recited in claim 1, wherein a silane functionalized end of said organic molecules is covalently attached to an gate dielectric located below said semiconductive film.

14. The transistor as recited in claim 1, wherein said semiconductive film further includes a linker molecule coupled to said organic molecule at said outer surface and coupled to one of said probe molecules.

15. The transistor as recited in claim 6, wherein a thiol-functionalized end of said linker molecule is covalently attached to a spacer group comprising an alkyl chain having up to 20 carbon atoms, and an other end of said spacer group is attached to one of said organic molecules.

* * * * *

UNITED STATES PATENT AND TRADEMARK OFFICE
CERTIFICATE OF CORRECTION

PATENT NO. : 7,189,987 B2
APPLICATION NO. : 10/405398
DATED : March 13, 2007
INVENTOR(S) : Zhenan Bao and Bernard Yurke It is certified that error appears in the above-identified patent and that said Letters Patent is hereby corrected as shown below:

Claim 5 should appear as follows:

5. The transistor as recited in claim ~~1~~ 4, wherein said organic molecules have a conjugated pi bond.

Claim 6 should appear as follows:

6. The transistor as recited in claim ~~1~~ 4, wherein said organic molecules are selected from the group consisting of polythiophene and oligothiophene.

Claim 7 should appear as follows:

7. The transistor as recited in claim ~~1~~ 4, wherein said semiconductive film is crystalline or polycrystalline.

Claim 8 should appear as follows:

8. The transistor as recited in claim ~~1~~ 4, wherein said semiconductive film comprises a monolayer of said organic molecules, wherein one end of said organic molecules is coupled to an gate dielectric located below said semiconductive film.

Claim 9 should appear as follows:

9. The transistor as recited in claim ~~1~~ 4, wherein said transistor channel is an active channel, and wherein said probe molecules are capable of binding to target molecules and are chemical bonded to said outer surface.

UNITED STATES PATENT AND TRADEMARK OFFICE
CERTIFICATE OF CORRECTION

PATENT NO. : 7,189,987 B2
APPLICATION NO. : 10/405398
DATED : March 13, 2007
INVENTOR(S) : Zhenan Bao and Bernard Yurke It is certified that error appears in the above-identified patent and that said Letters Patent is hereby corrected as shown below:

Claim 10 should appear as follows:

10. The transistor as recited in claim ~~1~~ 4, wherein said probe molecules are selected from the group consisting of: single stranded DNA; RNA aptamers; and proteins, and are configured to bind to biological target molecules selected from the group consisting of: cDNA; mRNA; and antibodies.

Claim 11 should appear as follows:

11. The transistor as recited in claim ~~1~~ 4, wherein binding a target molecule to said probe molecule results in a change in a conductivity or mobility of said channel.

Claim 12 should appear as follows:

12. The transistor as recited in claim ~~1~~ 4, wherein an amount of said probe molecules in said interior is less than or equal to a solubility of said probe molecule in said organic molecule.

Claim 13 should appear as follows:

13. The transistor as recited in claim ~~1~~ 4, wherein a silane functionalized end of said organic molecules is covalently attached to an gate dielectric located below said semiconductive film.

UNITED STATES PATENT AND TRADEMARK OFFICE
CERTIFICATE OF CORRECTION

PATENT NO. : 7,189,987 B2
APPLICATION NO. : 10/405398
DATED : March 13, 2007
INVENTOR(S) : Zhenan Bao and Bernard Yurke It is certified that error appears in the above-identified patent and that said Letters Patent is hereby corrected as shown below:

Claim 14 should appear as follows:

14. The transistor as recited in claim ~~1~~ 4, wherein said semiconductive film further includes a linker molecule coupled to said organic molecule at said outer surface and coupled to one of said probe molecules.

Claim 15 should appear as follows:

15. The transistor as recited in claim ~~6~~ 14, wherein a thiol-functionalized end of said linker molecule is covalently attached to a spacer group comprising an alkyl chain having up to 20 carbon atoms, and an other end of said spacer group is attached to one of said organic molecules.

Signed and Sealed this

Fifteenth Day of May, 2007

JON W. DUDAS
*Director of the United States Patent and Trademark Office*